US005691380A

United States Patent [19]

Mason et al.

[11] Patent Number: 5,691,380
[45] Date of Patent: Nov. 25, 1997

[54] STABLE N-ACETYLCYSTEINE COMPOSITIONS AND METHODS FOR TREATING HUMAN SKIN THEREWITH

[75] Inventors: Brent William Mason, West Chester; Joseph Michael Zukowski, Cincinnati; Larry Richard Robinson, Lebanon; Greg George Hillebrand, Fairfield, all of Ohio

[73] Assignee: The Procter & Gamble Company, Cincinnati, Ohio

[21] Appl. No.: 496,749

[22] Filed: Jun. 29, 1995

[51] Int. Cl.$^6$ .................................... A61K 31/23
[52] U.S. Cl. ...................... 514/562; 514/63; 514/937; 424/401
[58] Field of Search ................... 424/401; 514/562, 514/63, 937

[56] References Cited

U.S. PATENT DOCUMENTS

| | | | |
|---|---|---|---|
| 4,411,886 | 10/1983 | Hostettler et al. | 424/70 |
| 4,877,805 | 10/1989 | Kligman | 514/381 |
| 4,888,342 | 12/1989 | Kligman | 514/419 |
| 4,960,764 | 10/1990 | Figueroa, Jr. et al. | 514/63 |
| 5,091,171 | 2/1992 | Yu et al. | 424/642 |
| 5,296,500 | 3/1994 | Hillebrand | 514/562 |
| 5,385,938 | 1/1995 | Yu et al. | 514/557 |
| 5,389,677 | 2/1995 | Yu et al. | 514/557 |
| 5,411,991 | 5/1995 | Shander et al. | 514/665 |
| 5,451,405 | 9/1995 | Zhang et al. | 424/401 |

FOREIGN PATENT DOCUMENTS

| | | | |
|---|---|---|---|
| 0 330 369 A1 | 8/1989 | European Pat. Off. | A61K 7/48 |
| 358528 A2 | 3/1990 | European Pat. Off. | A61K 7/06 |
| 53-075339 A | 7/1978 | Japan | D21/16 |
| 95/34280 A1 | 12/1995 | WIPO | A61K 7/48 |
| 96/00060 A1 | 1/1996 | WIPO | A61K 31/195 |

OTHER PUBLICATIONS

G.H. Dahms et al., "New Formulation Possiblities Offered by Silicone Copolyols," *Cosmetics & Toiletries*, vol. 110, pp. 91–100, Mar. 1995.

M.E. Carlotti et al., "Optimization of W/O–S Emulsions and Study of the Quantitative Relationships Between Ester Structure and Emulsion Properties," *J. Dispersion Science and Technology*, 13(3), 315336 (1992).

P. Hameyer, "Comparative Technological Investigations of Organic and Organosilicone Emulsifiers in Cosmetic Water–in–Oil Emulsion Preparations," *HAPPI* 28(4) 1991, pp. 88–128.

J. Smid–Korbar et al., "Efficiency and usability of silicone surfactants in emulsions," Provisional Communication, *International Journal of Cosmetic Science*, 12, 135–139 (1990).

D.G. Krzysik et al., "A new Silicone Emulsifier for Water–in–Oil Systems," *Drug and Cosmetic Industry*, vol. 146(4), pp. 28–81 (Apr., 1990).

*Primary Examiner*—Rebecca Cook
*Attorney, Agent, or Firm*—David K. Dabbiere

[57] ABSTRACT

The present invention relates to topical compositions comprising N-acetylcysteine demonstrating improved odor stability. These compositions are useful for treating and visibly improving the appearance of human skin.

13 Claims, No Drawings

STABLE N-ACETYLCYSTEINE COMPOSITIONS AND METHODS FOR TREATING HUMAN SKIN THEREWITH

TECHNICAL FIELD

The present invention relates to topical compositions in the form of water-in-silicone emulsions comprising N-acetylcysteine. These compositions have improved stability as demonstrated by a lower incidence of malodor development. These compositions are useful for treating and visibly improving the appearance of mammalian skin. These compositions are especially useful for effacing and preventing wrinkles, improving the texture of the skin, removing unwanted hair from the skin, decreasing the pore size of the skin, moisturizing skin, and treating the histological changes associated with skin aging.

BACKGROUND OF THE INVENTION

Skin is subject to abuse by many extrinsic and intrinsic factors. Extrinsic factors include ultraviolet radiation, wind, low humidity, harsh surfactants, abrasives, and the like. Intrinsic factors include chronological aging and other biochemical changes from within the skin. Whether extrinsic or intrinsic, these abusive factors result in wrinkling and other histological changes associated with skin aging. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

These aging processes result in the thinning and general degradation of the skin. As the skin naturally ages, there is a reduction in the cells and blood vessels that supply the skin. There is also a flattening of the dermal-epidermal junction which results in weaker mechanical resistance of this junction. See, for example Oikarinen, "The Aging of Skin: Chronoaging Versus Photoaging," *Photodermatol. Photoimmunol. Photomed.*, vol. 7, pp. 3–4, 1990, which is incorporated by reference herein in its entirety.

Known anti-skin wrinkling agents include materials such as N-acetyl-L-cysteine, retinoids such as retinoic acid, and alpha-hydroxy acids such as glycolic acid and lactic acid. See, for example, U.S. Pat. No. 5,296,500, to Hillebrand, issued Mar. 22, 1994; U.S. Pat. No. 4,888,342, to Kligman, issued Dec. 19, 1989; U.S. Pat. No. 4,877,805, to Kligman, issued Oct. 31, 1989; U.S. Pat. No. 5,389,677, to Yu et at., issued Feb. 14, 1995; U.S. Pat. No. 5,385,938, to Yu et el., issued Jan. 31, 1995; and U.S. Pat. No. 5,091,171, to Yu et al., issued Feb. 25, 1992; which are all incorporated by reference herein in their entirety.

N-acetyl-L-cysteine is a preferred active of the present invention. However, this material is relatively labile. N-acetyl-L-cysteine tends to breakdown when it is formulated, releasing malodorous sulfur-containing compounds such as $H_2S$. This instability problem has limited the utility of formulating N-acetyl-L-cysteine into topical skin care compositions, especially those compositions intended to be applied to the face.

It has been surprisingly found in the present invention that compositions comprising N-acetylcysteine having improved stability can be achieved by utilizing a silicone-based emulsion system. Specifically, these compositions are in the form of water-in-silicone emulsions in which the silicone forms the continuous or external phase and the water forms the discontinuous or internal phase. These compositions exhibit a lower incidence of malodor development.

It is therefore an object of the present invention to provide topical compositions comprising N-acetylcysteine having improved stability.

It is another object of the present invention to provide topical compositions comprising N-acetylcysteine having a low incidence of malodor development.

It is another object of the present invention to provide topical compositions comprising N-acetylcysteine in the form of water-in-silicone emulsions.

It is another object of the present invention to provide a method for improving the stability of compositions comprising N-acetylcysteine.

It is another object of the present invention to provide a method for treating and visibly improving the appearance of human skin.

It is another object of the present invention to provide a method for effacing and reducing skin wrinkles, improving the texture of the skin, removing unwanted hair from the skin, decreasing the pore size of the skin, moisturizing the skin, and treating the histological changes associated with skin aging.

These and other objects of this invention will become apparent in light of the following disclosure.

SUMMARY OF THE INVENTION

The present invention relates to topical compositions comprising:

(a) from about 1% to about 60% of a silicone continuous phase comprising at least one liquid organopolysiloxane, (b) from about 30% to about 90% of an aqueous discontinuous phase comprising a safe and effective amount of a compound selected from the group consisting of N-acetylcysteine, derivatives of N-acetylcysteine, pharmaceutically-acceptable salts of N-acetylcysteine, pharmaceutically-acceptable salts of derivatives of N-acetylcysteine, and mixtures thereof, and (c) from about 0.1% to about 10% of an emulsifier.

In further embodiments, the present invention comprises methods for treating and visibly improving human skin comprising topically applying an effective amount of a composition comprising:

(a) from about 1% to about 60% of a silicone continuous phase comprising at least one liquid organopolysiloxane, (b) from about 30% to about 90% of an aqueous discontinuous phase comprising a safe and effective amount of a compound selected from the group consisting of N-acetylcysteine, derivatives of N-acetylcysteine, pharmaceutically-acceptable salts of N-acetylcysteine, pharmaceutically-acceptable salts of derivatives of N-acetylcysteine, and mixtures thereof, and (c) from about 0.1% to about 10% of an emulsifier.

All percentages and ratios used herein are by weight of the total composition and all measurements made are at 25° C., unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

The compositions of the present invention are useful for treating and visibly improving the appearance of mammalian skin, particularly human skin.

These compositions are in the form of water-in-silicone emulsions having a silicone continuous or external phase and an aqueous dispersed or internal phase. Silicone-containing emulsion compositions are well-known in the art, however, their utility for providing enhanced stability for labile, sulfur-containing actives such as N-acetylcysteine has until now been unknown. The following prior art references, which are all incorporated by reference herein in their entirety, disclose silicone-based emulsions systems: U.S. Pat. No. 4,960,764, to Figueroa, Jr. et al., issued Oct. 2, 1990; European Patent No. 330,369, to SaNogueria, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4) 1991, pp. 88–128; J. Smid-Korbar et al., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp.28–81 (April 1990).

The water-in-silicone compositions of the present invention comprising N-acetylcysteine and related compounds have improved stability, as demonstrated by a lower incidence of malodor formation. This stability is surprising because of the labile nature of active ingredients such as N-acetyl-L-cysteine.

The term "topical application", as used herein, means to apply or spread the compositions of the present onto the surface of the skin.

The term "pharmaceutically-acceptable," as used herein, means that the compositions or components thereof so described are suitable for rise in contact with human tissue without undue toxicity, incompatibility, instability, allergic response, and the like.

The term "safe and effective amount" as used herein means an amount of a compound or composition sufficient to significantly induce a positive therapeutic benefit, but low enough to avoid serious side effects, i.e. to provide a reasonable benefit to risk ratio, within the scope of sound medical judgment.

The term "chronic treatment" as used herein means continued topical application or treatment of the composition to the skin over an extended period during the subject's lifetime.

The term "treating and visibly improving the apearance of human skin" means that the compositions of the present invention are useful for topical application and provide benefits such as ameliorating the signs of skin aging, improving the texture of the skin, providing a depilatory effect for removing unwanted hair, decreasing pore size, and providing a skin lightening benefit on hyperpigmented spots and the like. "Signs of skin aging" includes, but is not limited to, all outward visible and tactilely perceptible manifestations, all internal manifestations, as well as any other macro or micro effects. For example, the term "skin aging" as used herein includes processes whether induced or caused by extrinsic factors or intrinsic factors. These processes include, but are not limited to the development of wrinkles, including both fine superficial wrinkles and coarse deep wrinkles, skin lines, sagging, discoloration, age spots, keratoses, hyperkeratinization, elastosis, collagen breakdown, and other histological changes in the stratum corneum, dermis, epidermis, the vascular system, and underlying tissues.

N-acetylcysteine

The aqueous phase of the compositions of the present invention comprise a safe and effective amount of N-acetylcysteine, derivatives of N-acetylcysteine, and pharmaceutically-acceptable salts thereof. The compositions of the present invention preferably comprise from about 0.01% to about 50%, more preferably from about 0.1% to about 10%, and most preferably from about 0.25% to about 5% of N-acetylcysteine. These weight percentages are based on the weight of the total composition.

N-acetylcysteine corresponds to the chemical formula $C_5H_9NO_3S$ and the following chemical structure:

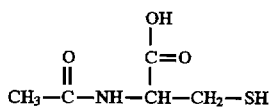

N-acetylcysteine is an "acetylated" derivative of the amino acid cysteine. Cysteine, and all amino acids more complex than glycine, exists as two enantiomeric forms, the naturally occurring "L" form and its non-naturally occurring "D" form. The "L" form of N-acetylcysteine, which is designated N-acety-L-cysteine, is preferred for use herein, because it is more readily available, although the "D" form can be used. It is also recognized that cysteine and its N-acetylated derivative can exist as an oxidized dimer, however, the monomeric form of N-acetylcysteine is preferred for use herein.

Also useful herein are derivatives of N-acetylcysteine. These derivatives include esters, amides, anhydrides, and thio-esters and thio-ethers of the sulfhydryl moiety. Non-limiting examples of these derivatives include: methyl N-acetylcysteine, ethyl N-acetylcysteine, stearyl N-acetylcysteine, N-acetylcysteine methylthioether, N,S-diacetylcysteine, N-acetylcysteine amide, and the mixed anhydride of N-acetylcysteine and acetic acid.

Also useful herein are pharmaceutically-acceptable salts of N-acetylcysteine and derivatives of N-acetylcysteine. Nonlimiting examples of these salts include sodium salts, potassium salts, magnesium salts, calcium salts, zinc salts, ammonium salts, alkyl ammonium and alkanol ammonium salts (in other words wherein the ammonium ion is substituted with one or more alkyl or alkanol moieties), and the like.

See The Merck Index, Tenth Edition, entry 82, page 13, (1983); and U.S. Pat. No. 5,296,500, to Hillebrand, issued Mar. 22, 1994; which are both incorporated by reference herein in their entirety.

Continuous Silicone Phase

The water-in-silicone emulsion compositions of the present invention comprise from about 1% to about 60%, more preferably from about 5% to about 40%, and most preferably from about 10% to about 20% of a continuous silicone phase comprising at least one liquid organopolysiloxane. In emulsion technology, the term "continuous phase" is a term well-known to one skilled in the art and means that the phase exists as the external phase and contains the discontinuous phase.

By "liquid" is meant a material having a melting point of about 25° C. or less at a pressure of about 1 atmosphere.

The liquid organopolysiloxane can be selected from a wide variety of silicones spanning a broad range of volatilities and viscosities. Examples of organopolysiloxanes include polyalkylsiloxanes, cyclic polyalkylsiloxanes, and polyalkylarylsiloxanes. The polyalkylsiloxanes useful herein include, for example, polyalkylsiloxanes with viscosities of from about 0.5 to about 1,000,000 centistokes at 25° C. Such polyalkylsiloxanes correspond to the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also, useful are dimethicones having pendant alkyl groups ranging from C2 to about C30, these materials can be designated by the formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Also useful herein are dimethiconols, which are hydroxy, terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

Dispersed Aqueous Phase

The water-in-silicone emulsion compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase.

The aqueous dispersed phase can simply be water, or water containing one or more soluble or dispersible pharmaceutically-acceptable ingredients. Nonlimiting examples of these pharmaceutically-acceptable ingredients include thickeners, acids, bases, salts, gums, water-soluble or dispersible alcohols and polyols, buffers, preservatives, sunscreening agents, colorings, antioxidants, and the like.

Emulsifier For Dispersing The Phases

The compositions of the present invention comprise from about 0.1% to about 10%, preferably from about 0.5% to about 7.5%, and more preferably from about 1% to about 5% of an emulsifier for dispersing the discontinuous aqueous phase into the continuous silicone phase.

A wide variety of emulsifying agents can be employed herein to form the water-in-silicone emulsions of the present invention. Mixtures of emulsifying agents are also useful. These emulsifiers include those selected from the group consisting of silicone emulsifiers, non-silicon-containing emulsifiers, and mixtures thereof. Preferably these emulsifiers have an HLB value of less than about 14, more preferably from about 2 to about 14, and most preferably from about 4 to about 14. It is found that emulsifiers having an HLB value outside of these ranges can be utilized if they are used in combination with other emulsifiers, so to achieve an effective weighted average HLB for the combination that falls within the ranges described in the previous sentence. The abbreviation, "HLB," stands for hydrophilic lipophilic balance. The HLB system is well known to one of ordinary skill in the art and is described in detail in "The HLB System, A Time-Saving Guide to Emulsifier Selection," ICI Americas Inc., August 1984, which is incorporated herein by reference in its entirety.

A wide variety of silicone emulsifiers are useful herein. These silicone emulsifiers are typically organically modified organopolysiloxanes. These materials are also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e. compounds which contain pendent C2–C30 pendant side chains. Still other useful dimethicone copolyols include materials having various cationic, anionic, amphoteric, and zwitterionic pendant moieties.

These dimethicone copolyols useful herein can be described by the following general structure:

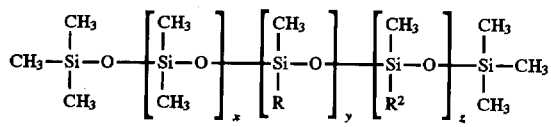

wherein R is C1–C30 straight, branched, or cyclic alkyl and $R^2$ is selected from the group consisting of —$(CH_2)_n$—O—$(CH_2CHR^3O)_m$—H, and

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is: ti —$(CH_2)_n$—O—$R^5$, wherein $R^5$ is a cationic, anionic, amphoteric, or zwitterionic moiety;

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemthicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993, which is incorporated by reference herein in its entirety.

The dimethicone copolyol emulsifiers useful herein are further described in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990); which have already been incorporated by reference herein in their entirety.

Among the non-silicon-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Additional Components

A wide variety of additional components can be employed in the topical skin compositions herein. Non-limiting examples include the following:

Zinc Salts

In preferred embodiments, the compositions of the present invention further comprise one or more zinc salts. Without being limited by theory, it is believed that the zinc provides an odor reduction benefit by complexing with $H_2S$ and other malodorous breakdown products of the N-acetyl L-cysteine.

When a zinc salt is present, the salt comprises from about 0.001% to about 10%, preferably from about 0.01% to about 5%, and most preferably from about 0.1% to about 0.5% of the compositions of the present invention.

Zinc salts useful in the present invention include, but are not limited to, the following: zinc acetate, zinc acetate hydrates such as zinc acetate-2-water, zinc aluminum oxide complexes such as gahnite, zinc diamine, zinc antimonide, zinc bromate hydrates such as zinc bromate-6-water, zinc bromide, zinc carbonates such as zincspar and smithsonite, zinc chlorate hydrates such as zinc chlorate-4-water, zinc chloride, zinc diamine dichloride, zinc chromate, zinc dichromate, zinc diphosphate, zinc hexacyanofluoride ferrate (II), zinc fluoride, zinc fluoride hydrates such as zinc fluoride-4-water, zinc formate, zinc formate hydrates such as zinc formate-2-water, zinc hydroxide, zinc iodate, zinc iodate hydrates such as zinc iodate-2-water, zinc iodide, zinc iron oxide complexes, zinc nitrate hydrates such as zinc nitrate-6-water, zinc nitride, zinc oxalate hydrates such as zinc oxalate-2-water, zinc oxides such as zincite, zinc perchlorate hydrates such as zinc perchlorate-6-water, zinc permanganate hydrates such as zinc permanganate-6-water, zinc peroxide, zinc p-phenolsulfonate hydrates such as zinc p-phenolsulfonate-8-water, zinc phosphate, zinc phosphate hydrates such as zinc phosphate-4-water, zinc phosphide, zinc propionate, zinc selenate hydrates such as zinc selenate-5-water, zinc selenide, zinc silicates such as zinc silicate (2) and zinc silicate (4), zinc silicon oxide water complexes such as hemimorphite, zinc hexafluorosilicate hydrates such as zinc hexafluorosilicate-6-water, zinc stearate, zinc sulfate, zinc sulfate hydrates such as zinc sulfate-7-water, zinc sulfide, zinc sulfite hydrates such as zinc sulfite-2-water, zinc telluride, zinc thiocyanate, zinc (II) salts of N-acetyl L-cysteine, and mixtures thereof.

Preferred zinc salts are those selected from the group consisting of zinc oxide, zinc chloride, zinc acetate, zinc stearate, zinc sulfate, and mixtures thereof. More preferred are those selected from the group consisting of zinc oxide, zinc chloride, and mixtures thereof. Most preferred is zinc oxide.

Sunscreens, Artificial Tanning Agents, and Skin Lightening Agents

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Preferred among those sunscreens which are useful in the compositions of the instant invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register.*, Vol. 43, No. 166, pp. 38206–38269, Aug. 25, 1978, which is incorporated herein by reference in its entirety.

Also useful in the present invention are sunless tanning agents including dihydroxyacetone, glyceraldehyde, indoles and their derivatives, phospha-DOPA, tyrosine, tyrosine esters such as ethyl tyrosinate, and the like.

Other useful actives include skin bleaching (or lightening) agents including but not limited to hydroquinone, ascorbic acid, kojic acid and sodium metabisulfite.

Humectants, Moisturizers, and Skin Conditioners

The compositions of the present invention can also comprise one or more humectant, moisturizing, or skin conditioning materials. A variety of these materials can be employed and each can be present at a level of from about 0.1% to about 20%, more preferably from about 1% to about 10%, and most preferably from about 2% to about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990, which is incorporated by reference herein in its entirety.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galaclose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Other Additional Components

The compositions of the present invention can comprise a wide range of other additional components. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, additional skin-conditioning agents, skin protectants, solvents, suspending agents (nonsurfactant), ultraviolet light absorbers, and viscosity increasing agents (aqueous and nonaqueous). Examples of other functional classes of materials useful herein that are well known to one of ordinary skill in the art include emulsifiers, solubilizing agents, sequestrants, and the like.

Nonlimiting examples of these additional components cited in the *CTFA Cosmetic Ingredient Handbook*, as well as other materials useful herein, include the following: water-soluble vitamins and derivatives thereof [e.g., vitamin C]; anti-oxidants; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; antioxidants; chelators and sequestrants. Also useful are crosslinked and noncrosslinked nonionic and cationic polyacrylamides [e.g., Salcare SC92 which has the CTFA designation polyquaternium 32 (and) mineral oil, and Salcare SC 95 which has the CTFA designation polyquaternium 37 (and) mineral oil (and) PPG-1 trideceth-6, and the nonionic Seppi-Gel polyacrylamides available from Seppic Corp.]. Also useful are crosslinked and uncrosslinked carboxylic acid polymers and copolymers such as those containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (examples useful herein include the carbomers, which are homopolymers of acrylic acid crosslinked with allyl ethers of sucrose or pentaerytritol and which are available as the Carbopol® 900 series from B. F. Goodrich, and copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol, these copolymers being known as acrylates/C10–30 alkyl acrylate crosspolymers and are commercially available as Carbopol® 1342, Pemulen TR-1, and Pemulen TR-2, from B. F. Goodrich). These carboxylic acid polymers and copolymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary*, fourth edition, 1991, pp. 12 and 80; which is also incorporated herein by reference. Also useful herein are aesthetic components such as fragrances, pigments, colorings, essential oils, skin senates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate and the like.

Methods for Treating and Visibly Improving the Appearance of Skin

The compositions of the present invention are useful for treating and visibly improving the appearance of human skin. The compositions are useful for reducing, effacing, and preventing wrinkles in human skin, improving the texture of the skin, removing unwanted hair from the skin, decreasing the pore size of the skin, moisturizing skin, and treating histological changes associated with skin aging. The methods of treatment comprise treating the skin with a safe and effective amount of the compositions of the present invention. The amount of the N-acetylcysteine active present in the composition and the frequency of treatment will vary widely depending upon the level of skin damage or aging present or the amount of hair to remove in the human subject, the rate of further skin aging or hair growth, and the level of regulation desired.

A preferred method of treating the skin is via chronic topical application. By "chronic application" is meant that the period of application can be over the lifetime of the subject, preferably for a period of about one week, more preferably for a period of about one month, even more preferably from about three months to about twenty years, even more preferably from about six months to about ten years, and more preferably still from about one year to about five years. Typically applications would be on the order of about once per day, however application rates can vary from about once per week up to about three times per day or more.

A wide range of quantities of the compositions of the present invention can be employed to provide a therapeutic benefit. Quantities of the present compositions which are typically applied to provide a benefit can range from about 0.1 mg/cm$^2$ to about 10 mg/cm$^2$. A particularly useful amount to use is about 2 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

Emulsion Composition

A water-in-silicone emulsion containing N-acetyl-L-cysteine is prepared by combining the following ingredients using conventional mixing techniques.

| Ingredients | Weight Percent |
| --- | --- |
| Water | qs 100 |
| Cyclomethicone[1] | 15.0 |
| Ethanol | 3.0 |
| Glycerin | 3.0 |
| Polyglyceryl-4 Isostearate (and) Cetyl Dimethicone Copolyol (and) Hexyl Laurate[2] | 2.50 |
| Cyclomethicone (and) Dimethicone Copolyol[3] | 2.50 |
| Hexylene Glycol | 2.0 |
| Sodium Hydroxide (50% by weight aqueous solution) | 0.95 |
| N-acetyl-L-cysteine | 2.00 |
| Tetrasodium EDTA | 0.50 |
| Benzyl Alcohol | 0.30 |
| Methyl Paraben | 0.20 |
| Citric Acid | 0.20 |
| Fragrance | 0.20 |
| Zinc Oxide | 0.10 |

[1]Dow Corning ® 345 fluid from Dow Corning.
[2]Abil WE-09 from Goldschmidt.
[3]Dow Corning ® 3225C from Dow Corning In a suitable vessel the methyl paraben, benzyl alcohol and ethanol are combined with mixing until a solution is obtained. Next, the water, glycerin, hexylene glycol, tetrasodium EDTA, citiric acid are added with mixing. Next, the N-acetyl-L-cysteine, zinc oxide, and sodium hydroxide are added in this order with mixing until dissolved. In a separate vessel, the cyclomethicone, polyglyceryl-4 isostearate (and) cetyl dimethicone copolyol (and) hexyl laurate, and cyclomethicone (and) dimethicone copolyol are first combined and then added with mixing to form the emulsion. Next the fragrance is added with stirring.

This N-acetyl-L-cysteine water-in-silicone emulsion is useful for topical application to human skin to treat and visibly improve the appearance of the skin. This emulsion demonstrates improved stability as demonstrated by reduced malodor formation.

Example 2

Emulsion Composition

A water-in-silicone emulsion containing N-acetyl-L-cysteine is prepared by combining the following ingredients using conventional mixing techniques.

| Ingredients | Weight Percent |
| --- | --- |
| Water | qs 100 |
| Cyclomethicone[1] | 13.0 |
| Ethanol | 3.0 |
| Glycerin | 3.0 |
| Polyglyceryl-4 Isostearate (and) Cetyl Dimethicone Copolyol (and) Hexyl Laurate[2] | 2.50 |
| Hexylene Glycol | 2.0 |
| Cyclomethicone (and) Dimethicone Copolyol[3] | 2.50 |
| Cyclomethicone (and) Dimethiconcol[4] | 2.00 |
| Sodium Hydroxide (50% by weight aqueous solution) | 0.95 |
| N-acetyl-L-cysteine | 2.00 |
| Tetrasodium EDTA | 0.50 |
| Benzyl Alcohol | 0.30 |
| Methyl Paraben | 0.20 |
| Citric Acid | 0.20 |
| Fragrance | 0.20 |
| Zinc Oxide | 0.10 |

[1]Dow Corning ® 345 fluid from Dow Corning.
[2]Abil WE-09 from Goldschmidt.
[3]Dow Corning ® 3225C from Dow Corning
[4]Dow Corning ® 1401 Substantivity Aid fluid from Dow Corning.

In a suitable vessel the methyl paraben, benzyl alcohol and ethanol are combined with mixing until a solution is obtained. Next, the water, glycerin, hexylene glycol, tetrasodium EDTA, citiric acid are added with mixing. Next, the N-acetyl-L-cysteine, zinc oxide, and sodium hydroxide are added in this order with mixing until dissolved. In a separate vessel, the cyclomethicone, polyglyceryl-4 isostearate (and) cetyl dimethicone copolyol (and) hexyl laurate, cyclomethicone (and) dimethiconol and cyclomethicone (and) dimethicone copolyol are first combined and then added with mixing to form the emulsion. Next the fragrance is added with stirring.

This N-acetyl-L-cysteine water-in-silicone emulsion is useful for topical application to human skin to treat and visibly improve the appearance of the skin. This emulsion demonstrates improved stability as demonstrated by reduced malodor formation.

Example 3

Emulsion Composition

A water-in-silicone emulsion containing N-acetyl-L-cysteine is prepared by combining the following ingredients using conventional mixing techniques.

| Ingredients | Weight Percent |
| --- | --- |
| Water | qs 100 |
| Cyclomethicone[1] | 15.0 |
| Ethanol | 3.0 |
| Glycerin | 3.0 |
| Polyglyceryl-4 Isostearate (and) Cetyl Dimethicone Copolyol (and) Hexyl Laurate[2] | 2.50 |
| Cyclomethicone (and) Dimethicone Copolyol[3] | 2.50 |
| Hexylene Glycol | 2.0 |
| Petrolatum | 1.5 |
| Sodium Hydroxide (50% by weight | 0.95 |

-continued

| Ingredients | Weight Percent |
| --- | --- |
| aqueous solution) | |
| N-acetyl-L-cysteine | 2.00 |
| Tetrasodium EDTA | 0.50 |
| Benzyl Alcohol | 0.30 |
| Methyl Paraben | 0.20 |
| Citric Acid | 0.20 |
| Fragrance | 0.20 |
| Zinc Oxide | 0.10 |

[1]Dow Corning ® 345 fluid from Dow Corning.
[2]Abil WE-09 from Goldschmidt.
[3]Dow Corning ® 3225C from Dow Corning In a suitable vessel the methyl paraben, benzyl alcohol and ethanol are combined with mixing until a solution is obtained. Next, the water, glycerin, hexylene glycol, petrolatum, tetrasodium EDTA, citric acid are added with mixing. Next, the N-acetyl-L-cysteine, zinc oxide, and sodium hydroxide are added in this order with mixing until dissolved. In a separate vessel, the cyclomethicone, polyglyceryl-4 isostearate (and) cetyl dimethicone copolyol (and) hexyl laurate, and cyclomethicone (and) dimethicone copolyol are first combined and then added with mixing to form the emulsion. Next the fragrance is added with stirring.

This N-acetyl-L-cysteine water-in-silicone emulsion is useful for topical application to human skin to treat and visibly improve the appearance of the skin. This emulsion demonstrates improved stability as demonstrated by reduced malodor formation.

What is claimed is:

1. A two phase water-in-silicone topical emulsion composition comprising:
   (a) from about 1% to about 60% of a silicone continuous phase comprising at least one liquid organopolysiloxane,
   (b) from about 30% to about 90% of an aqueous discontinuous phase comprising a safe and effective amount of a compound selected from the group consisting of N-acetylcysteine; a derivative of N-acetylcysteine selected from the group consisting of an ester of N-acetylcysteine, an amide of N-acetylcysteine, an anhydride of N-acetylcysteine, a thio-ester of N-acetylcysteine, and a thio-ether of the sulfhydryl moiety of N-acetylcysteine; a pharmaceutically acceptable salt of N-acetylcysteine; a pharmaceutically-acceptable salt of said derivative of N-acetylcysteine; or a mixture thereof, and
   (c) from about 0.1% to about 10% of an emulsifier for dispersing said discontinuous phase into said continuous phase.

2. A composition according to claim 1 comprising from about 0.01% to about 50%, based on the weight of the total composition, of the compound in the discontinuous phase.

3. A composition according to claim 1 comprising from about 0.1% to about 10%, based on the weight of the total composition, of the compound in the discontinuous phase.

4. A composition according to claim 1 comprising from about 0.25% to about 5% based on the weight of the total composition of the compound in the discontinuous phase.

5. A composition according to claim 2 wherein said liquid organopolysiloxane is selected from the group consisting of a polyalkylsiloxane, an alkyl substituted dimethicone, a cyclomethicone, a trimethylsiloxysilicate, a dimethiconol, and a polyalkylaryl siloxane, or a mixture thereof.

6. A composition according to claim 5 wherein said emulsifier is selected from the group consisting of a silicone emulsifier and a non-silicone-containing emulsifier, or a mixture thereof.

7. A composition according to claim 6 wherein said emulsifier is a silicone emulsifier.

8. A composition according to claim 7 wherein said silicone emulsifier corresponds to the following structure

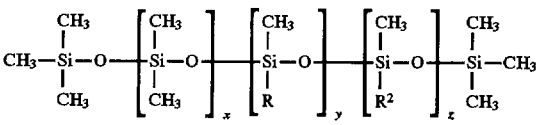

wherein R is C1–C30 straight, branched, or cyclic alkyl, $R^2$ is selected from the group consisting of

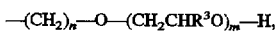

and

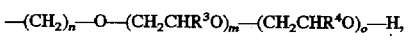

n is an integer from 3 to about 10; $R^3$ and $R^4$ are selected from H and C1–C6 straight or branched chain alkyl such that $R^3$ and $R^4$ are not simultaneously the same; and m, o, x, and y are selected such that the emulsifier molecule has an overall molecular weight from about 200 to about 10,000,000, with m, o, x, and y being independently selected from integers of zero or greater such that m and o are not both simultaneously zero, and z being independently selected from integers of 1 or greater.

9. A composition according to claim 8 wherein said emulsifier is cetyl dimethicone copolyol.

10. A composition according to claim 1 wherein said composition additionally comprises a zinc salt.

11. A composition according to claim 10 wherein said zinc salt comprises from about 0.001% to about 10% of said composition.

12. A composition according to claim 11 wherein said zinc salt is selected from the group consisting of zinc stearate, zinc sulfate, zinc chloride, and zinc acetate, or a mixture thereof.

13. A method for topically applying an effective amount of the composition of claim 1 to the skin.

* * * * *